United States Patent

Chinai et al.

[11] 3,976,075
[45] Aug. 24, 1976

[54] TAMPON BLANK WITH REDUCED SLOUGHING PROPERTIES

[75] Inventors: Kays Chinai, Burlington Township; Alfred Amend, Kendall Park, both of N.J.

[73] Assignee: Personal Products Company, Milltown, N.J.

[22] Filed: Feb. 24, 1975

[21] Appl. No.: 552,391

[52] U.S. Cl................. 128/285; 128/284; 128/290 P
[51] Int. Cl.².......... A61F 13/20; B32B 31/14
[58] Field of Search........ 128/284, 270, 285, 290 P, 128/290 B, 296, 285, 156; 428/196, 197, 198; 156/290, 291, 277

[56] References Cited
UNITED STATES PATENTS

| 2,328,795 | 9/1943 | Finks | 128/290 B |
|---|---|---|---|
| 2,442,937 | 5/1941 | Biederman | 128/285 |
| 2,553,000 | 5/1951 | Parish | 128/285 |
| 3,087,833 | 4/1963 | Drelich | 428/198 |
| 3,093,502 | 6/1963 | Drelich | 428/198 |
| 3,322,123 | 5/1967 | Griswold et al. | 128/285 |
| 3,428,044 | 2/1969 | Whitehead et al. | 128/285 |
| 3,553,065 | 5/1966 | Stumpf | 428/195 |
| 3,684,641 | 8/1972 | Murphy | 156/291 |
| 3,740,562 | 3/1973 | Drelich | 156/291 |
| 3,753,826 | 8/1973 | Plummer | 156/277 |
| 3,784,425 | 1/1974 | Schuster | 128/270 X |
| 3,828,783 | 8/1974 | Kennette | 128/284 |

Primary Examiner—Aldrich F. Medbery
Attorney, Agent, or Firm—J. Lipow

[57] ABSTRACT

Means are provided in an absorbent product, such as a catamenial tampon, for greatly reducing the tendency for fibrous particles to break loose from the body of the product during use, this condition being referred to as "sloughing". The means comprise a pad of absorbent material having printed on at least one surface thereof a non-occlusive pattern of adhesive binder. The pad, when used for a catamenial tampon, is turned upon itself into a generally cylindrical shape which may be compressed into the final tampon.

8 Claims, 12 Drawing Figures

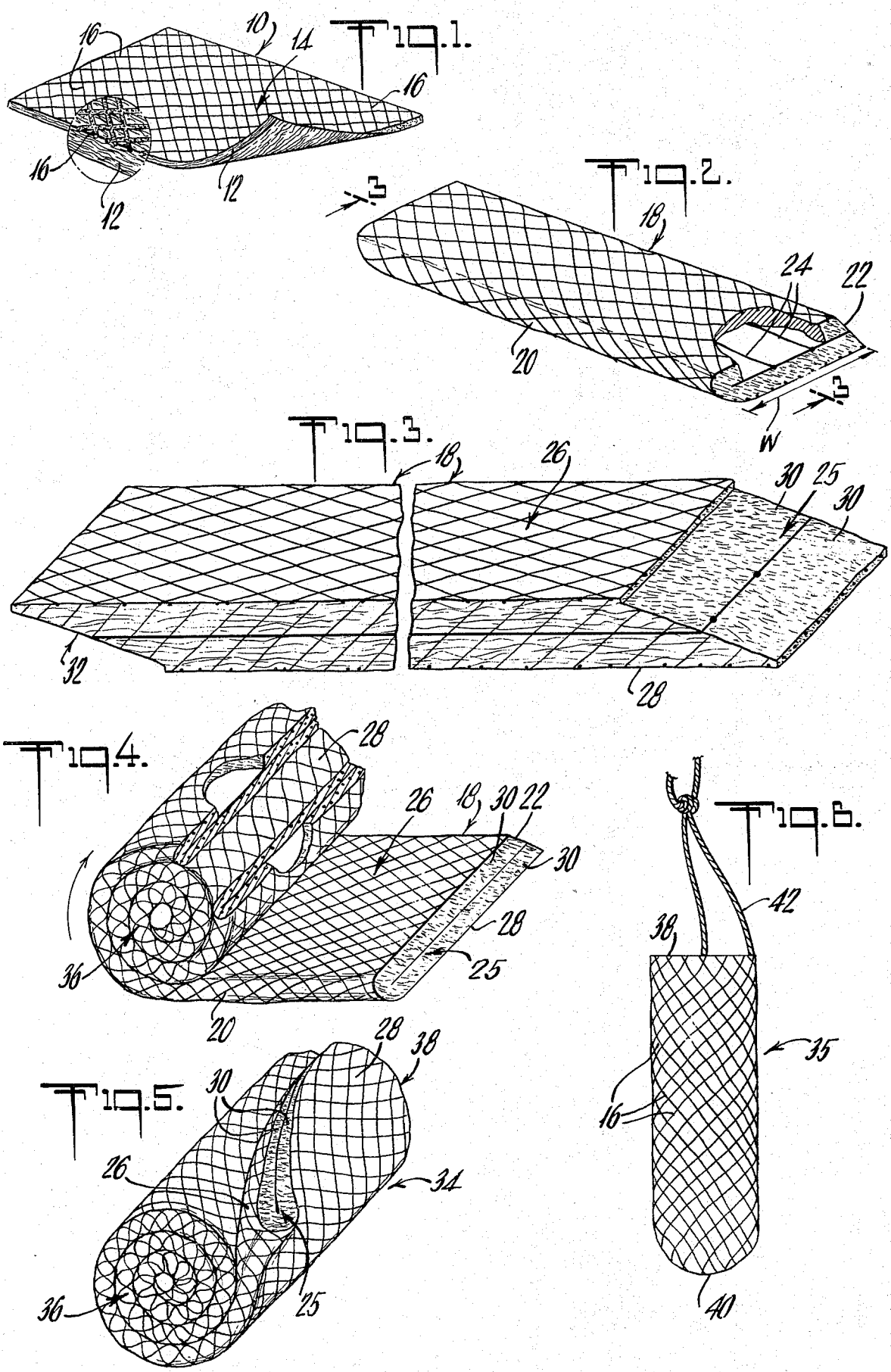

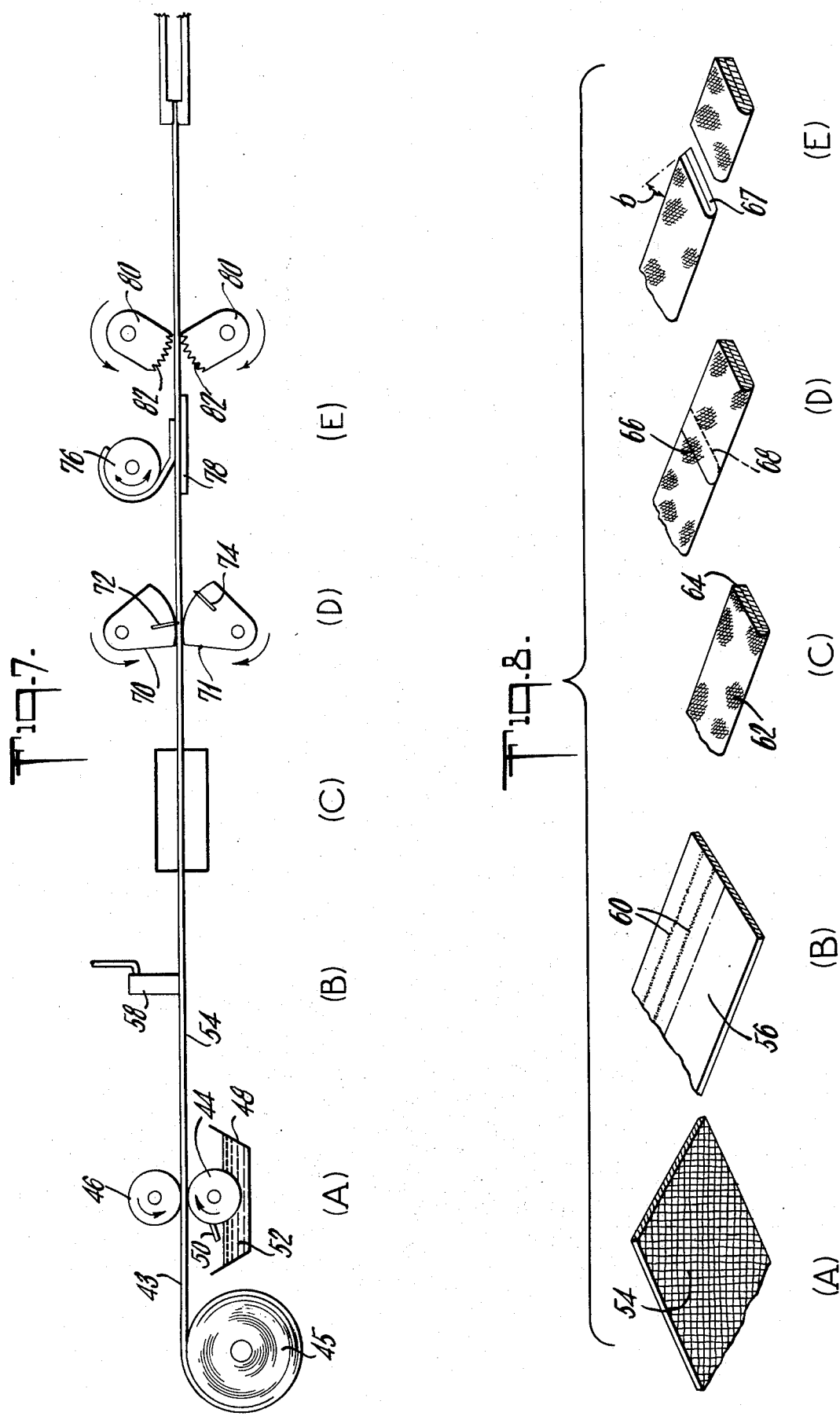

TAMPON BLANK WITH REDUCED SLOUGHING PROPERTIES

BACKGROUND OF THE INVENTION

This invention relates to absorbent products such as cosmetic wipes, sanitary napkins, diapers and catamenial tampons, comprising a pad of absorbent particulate matter. In the case of tampons, the pad is compressed into a desired, and generally cylindrical shape.

The aforementioned absorbent products in common use today are made up of absorbent particulate matter; most commonly of cellulosic fibers such as cotton, regenerated cellulose, i.e., rayon, and more recently of certain cellulosics which have been chemically modified to enhance their absorptivity, e.g., wet crosslinked cellulosics or grafted cellulose copolymers. Usually these fibers are formed into a loose, generally rectangular pad, and in the case of tampons, a withdrawal string is disposed around the pad and then the pad is wound or folded into the form of a blank which is then compressed in a die into the final tampon shape. In some cases, the blank or the compressed tampon is forced into a tampon applicator which is provided with a plunger and serves as a device for both retaining the tampon in the compressed form and for emplacing the tampon within the vagina of the user.

While, in the main, such tampons have been widely accepted and have functioned well, the art has been plagued by the problem known as sloughing. Sloughing, as related to tampons, is the release of particulate matter, and particularly fibers, from the surface of the tampon and the deposition of this released matter into the vagina. This release and deposition occurs primarily when inserting the dry tampon at which time frictional forces between the tampon and the walls of the vagina are greatest and tend to cause fibrous particulate matter to break loose.

Several methods have been suggested for alleviating the sloughing problem. Most commonly, the compressed tampon is provided with an outer cover of sheet material which is permeable to body fluids but which has sufficient wet strength to maintain its sheet-like integrity and act as an interface between the body of the tampon and the walls of the vagina. While this method is generally satisfactory, the incorporation of such a cover, usually comprised of such sheet material as nonwoven fabric, gauze and the like, has greatly impeded the high speed production of these tampons and, additionally, has added significantly to the cost of these tampons to the ultimate user. Further, under the stress imposed during use, not infrequently the cover material fails and not only does the cover then cease to be a shield against sloughing but instead actually adds to the problem by depositing pieces thereof in the vagina.

In view of the above problem, it has also been suggested, in U.S. Pat. No. 2,330,257, that the longitudinal sides of the tampon be provided with an occlusive, nonpermeable cover which has sufficient strength to insure that it will not come apart in use. While such a cover will in fact cure the problem with respect to cover failure, there is the concomitant drawback that those portions of the surface of the tampon so covered cannot transfer menses into the body of the tampon. Thus, any fluid which is not absorbed by the leading end of the tampon will remain unabsorbed.

In view of these drawbacks, it is apparent that no completely satisfactory solution has been heretofore provided for the sloughing problem.

SUMMARY OF THE INVENTION

In accordance with this invention, an absorbent product is provided which satisfactorily solves the sloughing problem without the concomitant drawbacks of increasing production or product costs and decreasing absorptivity, as have been associated with prior solutions. Specifically, this invention is directed to solving the sloughing problem in a product such as a tampon of the kind comprising a fibrous pad of absorbent material turned upon itself, as for example, by being folded or rolled into a generally cylindrical form and then compressed into a finished tampon. It has now been discovered that by providing the pad with a non-occlusive pattern of adhesive binder on at least one surface thereof, that surface being chosen as the surface which is at least partially exposed after the pad is turned upon itself into cylindrical form, the problem of sloughing is greatly alleviated. In contrast to prior art coating methods which tend to produce an occlusive coating on the sides of a tampon, in accordance with this invention, the adhesive binder is applied in a controlled pattern using methods such as, for example, printing, so that there is a substantial "open" or uncoated area. In this manner, the problem of sloughing is controlled and yet there is no significant reduction in the absorptivity of the tampon. While various patterns may be applied to the surface of the pad, it is preferred that the coated area be at least 5 percent and preferably no greater than 75 percent, based on the total area of the surface to which the adhesive is applied. Preferably, the coated area is from 10–60 percent.

In a more specific aspect of this invention, means are provided for substantially eliminating sloughing from the leading end of the tampon as well as the sides thereof. These means comprise providing a rectangular fibrous pad having a pattern of adhesive binder applied to one planar surface thereof, the pad being wider than the desired longitudinal length of the finished tampon. The pad is then folded longitudinally upon itself with the coated surface on the outside to produce a folded pad having both a folded longitudinal edge and an open longitudinal edge. The folded pad is then rolled in a direction parallel to the longitudinal edges and compressed into the finished tampon. In this manner, the folded longitudinal edge results in a leading end of the finished tampon which is coated with the non-occlusive adhesive pattern.

In still another aspect of the instant invention, means are provided for insuring that the pad, coated with the non-occlusive adhesive pattern as taught herein, does not unravel when rolled into cylindrical form and yet presents outside surfaces which are fully coated with the non-occlusive adhesive pattern. In particular, means are provided to insure that the trailing end of the pad on the outside of the roll remains adhered to the body of the roll and does not separate thereby unravelling the roll. The means comprise having this end of the pad cut on a bias so as to expose the loose fibers on the underside of the pad, i.e., that side which contacts the body of the roll. When the roll is then compressed, these loose fibers intermesh with the body of the roll to tightly adhere the trailing end to the finished tampon.

Ancillary to the reduction of the sloughing problem, it has been discovered that the tampons of this invention have other surprisingly improved functional characteristics. Specifically, it has been found that the tendency for "telescoping" has been greatly decreased. Telescoping as used herein is the tendency of tampons to unravel when subjected to the forces encountered during insertion and removal. By incorporating the teaching of this invention, such a tendency has been greatly decreased.

Further, it has been discovered that tampons made in accordance with the teaching of this invention have greatly increased abilities to withstand crushing forces, i.e., forces applied along the longitudinal axis of the tampon which would tend to buckle the same. This resistance to buckling is particularly important in connection with digitally inserted tampons where such forces are likely to be applied.

BRIEF DESCRIPTION OF THE DRAWINGS

FIG. 1 is a perspective view of a pad, with one corner turned up, and having printed thereon the non-occlusive adhesive binder in accordance with this invention, having a part thereof magnified;

FIG. 2 is a perspective view of a folded pad prior to rolling into a tampon and embodying the teachings of this invention;

FIG. 3 is a cross-sectional view of the folded pad of FIG. 2 taken along lines 3—3;

FIG. 4 is a perspective view of a partially rolled pad of the kind illustrated in FIGS. 3 and 4 with parts removed therefrom;

FIG. 5 is a perspective view of a completely rolled pad with a corner of the trailing end of the pad turned back;

FIG. 6 is an elevational view of a finished tampon embodying the teachings of this invention;

FIG. 7 schematically illustrates steps in making the rolled blank in accordance with this invention;

FIG. 8 schematically illustrates the work pieces as they pass through the steps shown in FIG. 7;

DETAILED DESCRIPTION OF THE INVENTION

Figure 9:
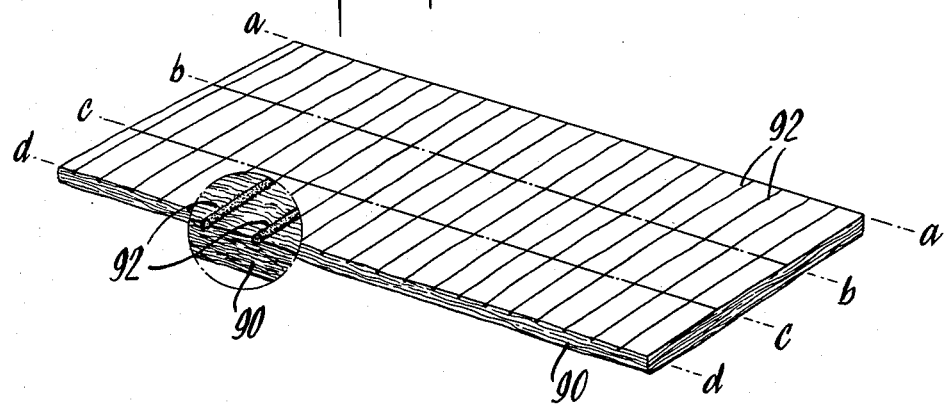
FIG. 9 is a perspective view of a pad having an alternatively printed pattern thereon and having a part thereof magnified.

Referring now to FIG. 1 of the drawings, illustrated therein is a pad 10 of absorbent material 12 such as for example, cellulose fibers, regenerated cellulose, modified cellulosics or combinations thereof and the like. While the pad may be a loosely compacted web of such material, preferably, the pad is composed of carded fibers having the fiber orientation in one direction. Printed onto a first surface 14 of the pad are lines 16 of a non-occlusive adhesive, the lines being in a spaced pattern so that no more than about 75 percent, of the total area of the surface 14 is occluded by the adhesive and preferably no more than about 60 percent. As is shown in FIG. 1, the pattern of adhesive is in the form of two sets of spaced parallel lines, each set being at an angle of approximately 90° to each other. It will be understood, however, that this invention is not limited in any way to this or any other particular pattern and so many variations will occur to one skilled in the art and still be within the teachings of the invention. For example, wavey, non-parallel lines may be used or even discontinuous spots of adhesive. The important consideration is that the adhesive be applied in a non-occlusive manner, i.e. leaving spaces therebetween, to preclude impairing the absorptivity of the resulting tampon to any substantial degree while still anchoring the absorbent particles or fibers at the surface of the pad so as to greatly reduce sloughing. Techniques for applying or printing adhesive onto a web in the grid-like pattern shown in FIG. 1 are already well-known and may be used in connection with this invention. For example, in U.S. Pat. No. 3,327,708, issued to R. C. Sokolowski on June 27, 1967, there is described a method for producing a printed pattern on a thin web for use as a wrapper on sanitary napkins and bandages, the disclosure of this patent being incorporated herein by reference. Briefly, this method utilizes an intaglio printing roll having the pattern desired embossed or etched therein. Still other useful printing methods are flexographic printing, where the adhesive is applied to the raised portions of a roll and then transferred to the web; reverse roll printing, where the adhesive is applied to a first roll having raised portions and then transferred to a second roll which in turn transfers the pattern to a web; and the like.

The adhesives employed herein should generally be non-allergenic, soft and flexible in both the wet and dry state and non-tacky when the tampon is in use. Additionally, the adhesives must be compatible with the printing system being employed, i.e., the adhesive should be capable of being dispersed in a suitable dispersing media, preferably water, to a concentration high enough to allow the printing rolls to deposit sufficient adhesive onto the pad and the emulsion should have a sufficiently low enough viscosity to allow the printing process to be carried out. Preferably, such an emulsion should carry at least 10 percent solids while having a viscosity of less than 1000 cps as measured by a Brookfield Viscometer at room temperature. A suitable deposition quantity is less than about 0.0050 gms. of adhesive solids/sq. cm. of surface coated with the adhesive. A preferable quantity is about 0.0005 gm. of adhesive solids/sq. cm.

Suitable adhesives may be olefinic, vinyl or acrylic polymers, copolymers or terpolymers, for example, polyacrylates, e.g., ethyl acrylate polymer; the block copolymers, e.g. carboxylated styrene-butadiene copolymers; the so-called plastisols which are colloidal dispersions of certain synthetic resins in a suitable organic ester plasticizer e.g., such resins as vinyl chloride with other vinyl resins plasticized by organic phthalates, sebocates, adipates, or phosphates. Also suitable are the polyamides, e.g. poly glycine, polyamino butaric acid, polyamino cupric acid; the polyoxides, e.g., polypropylene oxide, polyethylene oxide, these may be modified to include functional groups such as carboxylic, phosphoric sulphonic moieties; the ionic polyurethanes; and the cellulose derivatives, e.g., cellulose acetate, sulfate ethyl cellulose, hydroxy ethyl cellulose, carboxymethyl cellulose and the like.

Irrespective of the type of adhesive or the method of applying the same, the pad 10 of FIG. 1 is folded as shown in FIG. 2 to produce a folded pad 18 having a folded longitudinal edge 20 and an open edge 22. The folded edge 20 will become, as shall be described below, the leading end of the finished tampon. As shown in FIG. 2, the fold line is chosen such that the width of the folded pad, W, is approximately the desired length of the finished tampon. To result in a tampon having an essentially uniform density along its axial length, it is preferable that the unfolded pad 16 of FIG. 1 have a width which is approximately twice that of the desired length of the finished tampon and that the pad be then folded about a centrally located longitudinal fold line. To hold the pad folded in the configuration shown in FIG. 2, lines 24 of a suitable adhesive material may be applied to one or both of the inside surfaces and will preclude unintentional unfolding of the pad during further processing.

In accordance with one aspect of this invention, as best viewed in the cross-sectional view of folded pad 18 shown in FIG. 3, at least one end 25 of the folded blank is cut at a bias so that the printed surface on one side 28 of the folded pad extends beyond the printed surface on the opposite side 26 and the fibrous absorbent material 30 at this end of the pad are exposed and project from this end beyond the shorter printed surface. Because it is contemplated that multiple pads will be cut from a longitudinally extending folded pad, a corresponding bias cut is illustrated on the other end 32 of the folded pad.

It will be understood by one skilled in the art that while the bias cut illustrated in FIG. 3 presents a straight line edge angled diagonally from surfaces 26 and 28, it is not essential to use such a straight line cut and curved or other configurations are equally satisfactory.

The folded pad 18 is then rolled into spiral form by starting at end 32, rolling the pad in a longitudinal direction while maintaining the shorter surface 26 (i.e., shorter with respect to end 25) on the inside of the spiral. A partially rolled folded pad is illustrated in FIG. 4 and a completely rolled pad is illustrated in FIG. 5. It should be noted, in connection with these figures, that, by virtue of the folded edge 20, one end 36 of the resulting rolled pad 34 which will correspond to the leading end of the finished tampon is completely covered at its exposed surface by the printed pattern. Similarly, the entire remaining outer surface of the rolled pad is covered by the printed pattern with the exception of the end 38 corresponding to the open edge 22 of the folded pad. This latter end 38 will, of course, ultimately become the withdrawal end of the tampon.

As shown in FIGS. 4 and 5, the bias cut end 25 becomes the trailing end of the folded pad disposed on the exterior of the completely rolled folded pad. By virtue of the bias cut, the inside surface of the end 25 has exposed fibers 30 which then contact the outer surface of the roll and intermesh therewith to adhere this trailing end 25 onto the surface of the roll. As viewed in FIG. 5, it should be noted that because of the bias cut, the surface 28 is longer at this end then the inner surface 26, and, hence, after the edge 24 is pressed into place, the intermeshing fibers 30 are not exposed on the exterior surface of the rolled pad, but, instead, the rolled pad presents a uniformly covered surface. If desired, the adherence of the trailing end 25 can be further assured by applying thereto small quantities of a suitable adhesive such as carboxymethyl cellulose.

The rolled pad of FIG. 5 is then compressed either longitudinally, radially or both, into the final tampon 35 illustrated in FIG. 6 having a leading end 40, and a withdrawal end 38 with a withdrawal string 42 extending therefrom in the usual manner for tampons. The withdrawal string may be sewn through the tampon or attached in any of the many ways already known in the art. For example, the withdrawal string could be looped or tied around the folded pad prior to rolling and compressing. It will be noted that the finished tampon has all surface which will come into frictional contact with the walls of the vagina fully covered with the printed pattern of adhesive. The withdrawal end 38, the only end uncovered by this pattern, will of course, make only minimal contact with the vagina walls and, hence, it is not disadvantageous to have this end uncovered.

Illustrated in FIG. 7 is a schematic representation of a part of a manufacturing line for producing the tampons of this invention. FIG. 8 schematically illustrates the condition of the work piece as it passes each of the various work stations shown in FIG. 7. A long web 43 of carded absorbent fibers is passed from a supply roll 45 to a printing station (A) comprising printing roller 44, back-up roller 46, adhesive composition reservoir 48 and doctor blade 50. The adhesive composition reservoir contains a supply of adhesive 52, preferably in aqueous emulsion form. The printing roll is provided with grooves etched into the surface thereof in the desired printing pattern and is rotated, first into the composition held in the reservoir to coat the roll surface, then past the doctor blade 50 where the blade wipes the roll surface clean of excess adhesive composition leaving adhesive in essentially only the etched grooves. The printing roll then further rotates onto the passing web, imprinting the adhesive pattern onto one surface 54 thereof. FIG. 8(A) illustrates the printed surface of the carded web as it leaves the printing station.

The printed web next passes under an adhesive application station (B), where two lines of adhesive 60, as illustrated in FIG. 8(B) are applied via adhesive applicator 58 to the surface 56 opposite the printed surface 54. As described above, these adhesive lines will facilitate handling of the web after it is folded. The web next proceeds to a folding station (C) where it is folded along a line approximately centrally located with respect to the longitudinal edges of the web and parallel therewith to produce a folded web, as is illustrated in FIG. 8(C), having a folded edge 62, an open edge 64 and having the unprinted surface 56 in the interior of the fold. The folded web next proceeds to a notching station (D) where, as illustrated in FIG. 8(D), notches 66, 68 are cut along the cross direction of the folded web and into both the top and bottom surfaces thereof. The notches on each of the surfaces are offset from each other by a distance, in the machine direction, such that the plane containing both notches forms an angle with the plane of the folded web which angle is the desired angle at which the trailing end of the pad is to be biased. The notches are cut to a depth in each surface at least sufficient to pass through the printed lines of adhesive and which need not be significantly deeper. The notching is accomplished by passing the web through two notching rolls 70, 71 each comprising a knife 72,74; the knives being separated, in time-sequence, to produce the required notch offset. Because of this separation, each knife may utilize the opposed notching roll as an anvil during the notching process. The notched web then passes the web severing station (E) where the web is severed into individual pads, each having a severed end 67 at the required bias angle (b). The severing is accomplished by passing the web between a rotary clamp 76 and a clamp table 78 which is in the open position and is upstream of a pair of eccentric nips 80. When the web has proceeded to a point where the notches are between the clamping table and the nips, the rotary clamp 76 has turned to a position whereby the web is held firmly clamped to the clamping table 78. At this point, the eccentric nips 80 have rotated to a position where the teeth 82 grip the web. As the nips 80 continue to rotate, the web is severed at the notches into individual pads by a pulling action between clamp and the nips, thus tearing loose fibers in the area of the biased end of the pads. As described above, these loose fibers, in accordance with this invention are desirable in that, when the pad is rolled into a tampon blank form, the loose fibers in the trailing end of the pad intermesh with the exterior surface of the roll and are thereby held securely in place after the roll is compressed into the finished tampon form.

Figure 10:
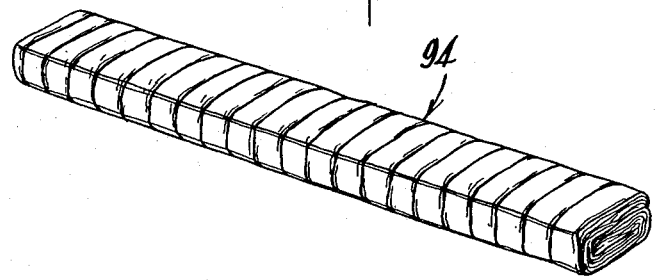
FIG. 10 is a perspective view of a partially folded blank made by folding the pad of FIG. 9.
Figure 11:
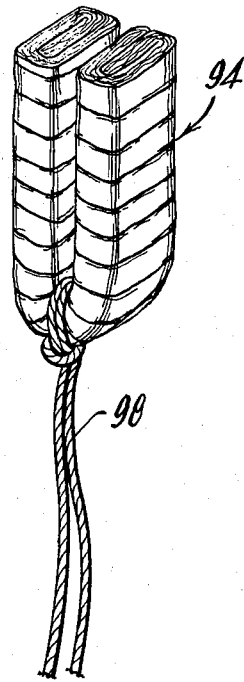
FIG. 11 is a perspective view of a completely folded blank.
Figure 12:
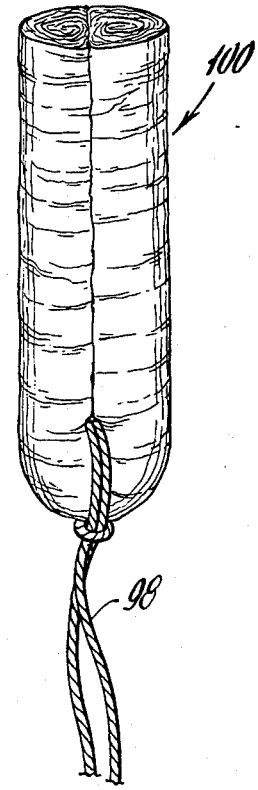
FIG. 12 is an elevational view of a finished tampon made from the blank of FIG. 11.

Referring now to FIG. 9, illustrated therein is a second pad 90 which may comprise the absorbent materials described above and which is printed with the same adhesive materials described above in a non-occlusive pattern which, in this case, is a pattern of parallel adhesive lines 92 running essentially perpendicular to the longitudinal edges of the pad. The pad is turned upon itself to form the folded blank 94 shown in FIG. 10 by first folding longitudinal edge *a* toward fold line *c* by folding at line *b*. The folding process is continued in the same direction (toward edge *d*) by folding at line *c* and thereby forming a longitudinally extending folded pad having three layers of the absorbent material. This pad is next folded into a U-shaped blank 94 as shown in FIG. 11. The blank 94 may be compressed by placing it into an appropriately shaped die or by forcing it into a tampon applicator or both and in its finished form will take the shape of the final tampon 100 illustrated in FIG. 12. A withdrawal string 98 is applied thereto in the usual manner and, for this particular embodiment, is best applied by either looping or tieing a string about the crotch portion of the U-shaped blank prior to forming the final tampon.

It will be apparent that, while two specific embodiments are described above, many other ways of turning the pad upon itself, including various combinations of folding and/or rolling steps, will occur to one skilled in the art and still be within the scope and spirit of the invention described herein.

EXAMPLE 1

A series of tampons are prepared using the methods of this invention as described above. In each case, the tampons are formed from a rectangular pad having the general configuration shown in FIG. 3 and measuring 8.5 inches in length, and 1.9 inches in width. The pad, comprising carded three denier rayon fibers having an average staple length of 1⅛ inches are printed with an adhesive pattern using the methods described above. The adhesive employed is a carboxylated styrene-butadiene adhesive comprising 65 percent styrene and 35 percent butadiene, by weight, and has a glass transition temperature of −6°C. The adhesive is applied to the pad, using the methods described in connection with FIGS. 7 and 8 of the drawings, from a water-based, 50 percent solids emulsion. A quantity of 0.0005 gm. solids/sq. cm. are applied to the printed surface in a pattern of lines each having a width of about 17 mil. The pattern is varied to produce samples of varying adhesive coverage of from about 0–49 percent coverage, based on the area printed, as reported in Table I which follows. The 49 percent coverage samples have printed thereon a pattern comprising two sets of parallel lines spaced at five lines per inch, each set forming a 30° angle with the longitudinal edge of the pad, the sets sloping in opposite direction, however, so as to intersect and form a diamond-shaped pattern. The 37 percent coverage samples have the same pattern as described above with the exception of having four lines per inch. The 25 percent coverage samples have a pattern of parallel lines, 17 mil thick and five lines per inch, the lines running at 90° with the longitudinal edge of the pad. The 17.5 percent coverage samples are identical to that of the 25 percent samples with the exception that four lines per inch are employed. The pads in accordance with the teachings of this invention, having the biased endings, are folded along their longitudinal center line and rolled in a direction parallel to their longitudinal edges as described above, and compressed into an essentially cylindrical tampon shape having a diameter of about 0.58 inches and a length of about 1.88 inches, this size corresponding to the so-called "super" sized tampons now being sold by the Personal Products Company of Milltown, N.J., under the trademark "CAREFREE". Data corresponding to a super CAREFREE tampon is likewise included in Table I, as a control and denoted as having zero percent coverage. The tampons made from the pattern printed pads are covered on all external surfaces with the pattern, with the exception of the withdrawal end and, by virtue of the bias end, present a smooth continuous outer surface appearance.

A second series of tampons are likewise prepared, identical in all respects to that of the samples described above as having 30 percent coverage with the exception that this second series utilizes a slightly smaller pad and hence, produces tampons having a diameter of about 0.51 inch and a length of about 1.85 inches which size corresponds to the size of "regular" CAREFREE tampons, also sold by Personal Products Company. For comparison purposes, data corresponding to regular CAREFREE tampons have been included in Table I following, as a control and denoted as having zero percent coverage.

The above described tampons are subjected to a sloughing test designed to quantify the in-use sloughing propensity of a tampon. The samples are first conditioned by maintaining them for a period of 48 hours in an environment controlled at 65 percent relative humidity and 72°F. A sample being tested is then placed between two layers of flexible abrasive material measuring 11 by 1¾ inches and consisting of polyurethane foam sold by General Foam Inc. of New Jersey, under the code number 4400. The sample is placed between the layers with its longitudinal axis parallel to the longitudinal axis of the layers and with the insertion end of the tampon essentially at one transverse edge of the layers. The withdrawal string then extends toward the opposite transverse end of the layers. The sample, so sandwiched between the abrasive layers is placed in the tester which comprises a glass cylinder lined with a polyethylene flexible sleeve. Means are provided for applying and maintaining air pressure to the annular space between the glass cylinder and the sleeve. Air pressure is so applied as to produce a pressure, on the sample, equivalent to 8 inches of water, gauge. The withdrawal string from each sample is then attached to a motor driven assembly and the tampon is pulled through the abrasive layers at a speed of 1.2 inches/second. The weight of the tampon prior to and after testing is recorded and the condition of the tampon after testing is noted, with respect to telescoping. Telescoping, as used herein, means that the spiral of the rolled pad has become essentially entirely unwound in the course of the sloughing test. The results of the sloughing test is reported in Table I.

TABLE I

SLOUGHING TEST

| Sample | Area Coverage (%) | Nos. of Tampons Tested | Average Wt. Before Test (gm.) | Average Wt. Loss After Test (mg.) | Nos. of Tampons Telescoped |
|---|---|---|---|---|---|
| | "Super" Tampons — 0.58 in dia., 1.88 in. length | | | | |
| 1 | 0 | 10 | 3.93 | 37.9 | 2 |
| 2 | 17.5 | " | 3.92 | 24.0 | 0 |
| 3 | 25 | " | 3.92 | 6.3 | 0 |
| 4 | 37 | " | 3.92 | 3.2 | 0 |
| 5 | 49 | " | 3.86 | 4.0 | 0 |
| | "Regular" Tampons — 0.51 in. dia., 1.85 in. length | | | | |
| 6 | 0 | " | 2.97 | 26 | 4 |
| 7 | 49 | " | 3.13 | 1.2 | 0 |

TABLE II

| Sample | Area Coverage (%) | CRUSH TEST Tampon Weight (Gms) | Crush Strength (Kg.) |
|---|---|---|---|
| 1 | 0 | 3.73 | 2.15 |
| 2 | 37 | 3.76 | 5.52 |
| 3 | 49 | 3.88 | 6.56 |

As is clearly illustrated by the above data, telescoping only occurs in tampon samples having zero percent coverage and those tampons made in accordance with the teachings of this invention have essentially eliminated the problem completely. While the reasons for this are not clearly understood, it is believed that the face-to-face relationship of coated surfaces which exists between adjacent spirals of the rolled pads in the tampons of this invention cause, to a degree, an interlocking between these adjacent spirals and this gives the rolled form greater structural integrity.

With respect to sloughing, it can be seen that even the minimal area coverage prescribed herein substantially reduces the weight loss encountered during the sloughing test. Increasing the area coverage to even a moderate percentage (25.0 percent) has the surprisingly dramatic effect of reducing sloughing by a factor of six. Still greater coverage, produces an order of magnitude reduction in sloughing.

EXAMPLE 2

A series of super sized tampons are prepared in accordance with the foregoing example and are tested to determine their columnar resistance or crushing resistance. Each tampon tested is placed in a vertical position on a flat plate held on the lower jaw of an Instron Universal Tester. The upper jaw is then brought to bear upon the tampon at a rate of 2 inches per minute and the maximum force exerted upon the tampon as it deforms is recorded as the Crush Strength in Table II which follows. For comparative purposes, data corresponding to that of a super CAREFREE tampon, having zero area coverage, is likewise reported in Table II.

As Table II clearly indicates, the resistance to crushing for tampons made in accordance with the teachings of this invention is more than twice that of the commercial control tampon for a 37 percent area coverage and more than three times for a 49 percent area coverage.

EXAMPLE 3

A series of super sized tampons are prepared as in the foregoing examples and are tested to determine their absorption properties. The capacity of these tampons to absorb a 1 percent by weight aqueous sodium chloride solution (approximating the salt content of menstrual fluid) under simulated in-use conditions is determined by allowing one end of the sample tampon to be submerged in the solution for a period of 20 minutes while maintaining the sides of the tampon under a confining of 8 inches of water, maintained by enveloping the tampon in a hydraulically inflated polyethylene sleeve. Excess fluid is drained from the tampon, the pressure is released and the weight of solution absorbed by the tampon is determined and reported in Table III below as both the average tampon capacity and as the ratio of average capacity to weight of the tampon. In addition to capacity, the rate of absorbency of tampons is likewise measured using the Absorbency Time for Nonwoven Fabrics Test of the American Society for Testing Materials (ASTM D-1117). Generally, this test involves placing a sample, snugly held in a basket and then placing this basket in a beaker of liquid so that the basket floats freely on the surface of the liquid. The time required for the basket to sink is taken as a measure of the rate of absorbency. In this particular example, in each case, a five gram sample of the variously printed pads is rolled, printed patterns on the exterior surface, and placed snugly in the basket. An unprinted pad, designated as 0 percent coverage, is used as a control. The results are likewise reported in Table III.

TABLE III

| SAMPLE | AREA COVERAGE (%) | TAMPON WEIGHT (gms) | Absorption Test TAMPON DENSITY grains/in$^3$ | CAPACITY (cc) | RATIO (cc/gm) | ABSORBENCY TIME (Seconds) |
|---|---|---|---|---|---|---|
| 1 | 0 | 3.80 | 110.9 | 14.8 | 3.91 | 1.7–2.2 |
| 2 | 17.5 | 3.76 | 114.5 | 15.8 | 4.20 | 2.0 |
| 3 | 25 | 3.76 | 118.2 | 14.7 | 3.96 | 2.0 |
| 4 | 37 | 3.81 | 115.1 | 15.2 | 3.99 | 2.5 |

TABLE III-continued

| SAMPLE | AREA COVERAGE (%) | TAMPON WEIGHT (gms) | TAMPON DENSITY grains/in³ | Absorption Test CAPACITY (cc) | RATIO (cc/gm) | ABSORBENCY TIME (Seconds) |
|---|---|---|---|---|---|---|
| 5 | 49 | 3.86 | 120.2 | 15.3 | 3.96 | 3.5 |

As the foregoing table indicates, there is little effect upon the capacity of the tampons to absorb fluid notwithstanding the presence of even a substantial degree of printed adhesive coverage. For the most part, there is also little effect in the rate of absorption as determined by the absorbency time, however, as the area coverage reaches the 49 percent value, there is a slight increase in the absorbency time, although it should be understood that even at this condition, the absorbency rate is tolerable.

The invention has been described above in terms of a catamenial tampon. It should be understood however, that the teachings herein are broadly applicable to any absorbent product comprising a pad of particulate matter such as fibers, powders and the like, where sloughing is a problem. Thus, it will be clear that the invention is applicable to cosmetic wipes and that by providing a pad of absorbent particulate matter such as absorbent fibers with a non-occlusive pattern of adhesive binder printed on at least one surface thereof, the problem of sloughing related to this product will be greatly reduced. Similarly, the invention is applicable to other absorbent products such as dressings, sanitary napkins, and diapers and a pad of absorbent fibers provided with a non-occlusive pattern of adhesive binder printed thereon will greatly alleviate the problem of sloughing in products of this nature as well.

What is claimed is:

1. A catamenial tampon blank for producing a finished tampon, said blank comprising a pad of absorbent material turned upon itself wherein means are provided for reducing sloughing from the outside surface of the tampon and for reducing telescoping of the tampon, said means comprising having printed on at least one pad surface a non-occlusive pattern of adhesive binder, a part of said printed pad surface being that which forms at least a part of the outside surface of the blank, the remainder of said printed pad surface being in the interior of said blank.

2. The tampon blank of claim 1 wherein the printed pattern is applied so that the adhesive binder coats at least about 5 and not more than about 75 percent of the total printed surface.

3. The tampon blank of claim 2 wherein the adhesive coats at least about 10 and more than about 60 percent of the printed surface.

4. The tampon blank of claim 2 wherein the adhesive comprises a styrene-butadiene adhesive.

5. The tampon blank of claim 2 wherein the adhesive comprises a carboxymethyl cellulose adhesive.

6. The tampon blank of claim 1 wherein means are provided to reduce sloughing from the leading end of the tampon, said means comprising having said pad folded longitudinally upon itself so as to form a folded pad having a longitudinal open edge, a longitudinal folded edge with said printed pattern on the exposed major surfaces of said folded pad and then having said pad rolled in a direction parallel to the longitudinal edges to form said blank.

7. The tampon blank of claim 6 wherein means are provided for adhering the trailing end of said folded, rolled pad to the exterior surface of the blank, said means comprising having said end contain exposed loose fibers which intermesh with said exterior surface.

8. The tampon of claim 6 wherein means are provided for insuring that the exterior surface of the blank is essentially fully covered by said non-occlusive pattern, said means comprising having said trailing end of said folded rolled pad cut at a bias so that said loose fibers are exposed essentially only on the underside of said trailing end.

* * * * *